(12) United States Patent
Gilpatrick, Jr. et al.

(10) Patent No.: US 10,034,660 B2
(45) Date of Patent: Jul. 31, 2018

(54) SPECIMEN COLLECTION KIT

(71) Applicant: Cahill Swift, LLC, Boston, MA (US)

(72) Inventors: George Y. Gilpatrick, Jr., Boston, MA (US); Joseph H. Lofgren, Minneapolis, MN (US)

(73) Assignee: Cahill Swift, LLC, Boston, MA (US)

( * ) Notice: Subject to any disclaimer, the term of this patent is extended or adjusted under 35 U.S.C. 154(b) by 0 days.

(21) Appl. No.: 15/256,078

(22) Filed: Sep. 2, 2016

(65) Prior Publication Data
US 2017/0055959 A1    Mar. 2, 2017

Related U.S. Application Data

(60) Provisional application No. 62/213,616, filed on Sep. 2, 2015.

(51) Int. Cl.
| | |
|---|---|
| *A61B 10/00* | (2006.01) |
| *B01L 9/06* | (2006.01) |
| *B01L 3/00* | (2006.01) |
| *A61B 90/50* | (2016.01) |
| *A61B 90/00* | (2016.01) |

(52) U.S. Cl.
CPC .......... *A61B 10/0096* (2013.01); *A61B 90/50* (2016.02); *B01L 9/06* (2013.01); *A61B 2090/081* (2016.02); *B01L 3/5082* (2013.01); *B01L 2200/02* (2013.01); *B01L 2200/141* (2013.01); *B01L 2300/0832* (2013.01); *B01L 2300/123* (2013.01)

(58) Field of Classification Search
CPC ...... B01L 3/5082; B01L 9/06; A61B 10/0096; A61B 90/50

USPC .......................................................... 422/430
See application file for complete search history.

(56) References Cited

U.S. PATENT DOCUMENTS

| | | | | |
|---|---|---|---|---|
| 5,725,109 | A | * 3/1998 | Moulton ................... | B01L 9/06 211/73 |
| 2003/0012701 | A1* | 1/2003 | Sangha ............ | A61B 5/150022 422/400 |
| 2003/0100881 | A1* | 5/2003 | Hwang ............ | A61B 5/150732 604/403 |
| 2003/0232451 | A1* | 12/2003 | Casterlin .............. | A61B 10/007 436/514 |
| 2010/0119417 | A1* | 5/2010 | Motadel ................... | B01L 3/00 422/400 |
| 2013/0313296 | A1* | 11/2013 | Stewart ..................... | A45F 3/00 224/218 |

(Continued)

FOREIGN PATENT DOCUMENTS

EP    0832689    * 4/1998

*Primary Examiner* — Jill A Warden
*Assistant Examiner* — Jacqueline Brazin
(74) *Attorney, Agent, or Firm* — The Bruttomesso Law Office; Raymond I. Bruttomesso, Jr.

(57) ABSTRACT

A method and system for collection of a specimen includes a specimen collection kit. The specimen collection kit includes a collection container adapted to receive the specimen, and a specimen bottle adapted to receive the specimen from the collection container. The kit has a specimen bottle holder having a planar plate with a bottle-receiving opening to receive the specimen bottle. The specimen bottle holder has a curvature such that a pair of edges of the planar plate are adapted to engage a surface therein spacing the bottle-receiving opening from the surface.

14 Claims, 10 Drawing Sheets

(56) References Cited

U.S. PATENT DOCUMENTS

2013/0344614 A1* 12/2013 Lucke ..................... B01L 3/52
  436/174
2015/0225158 A1*  8/2015 Lyzenga .............. B65D 75/527
  206/476

* cited by examiner

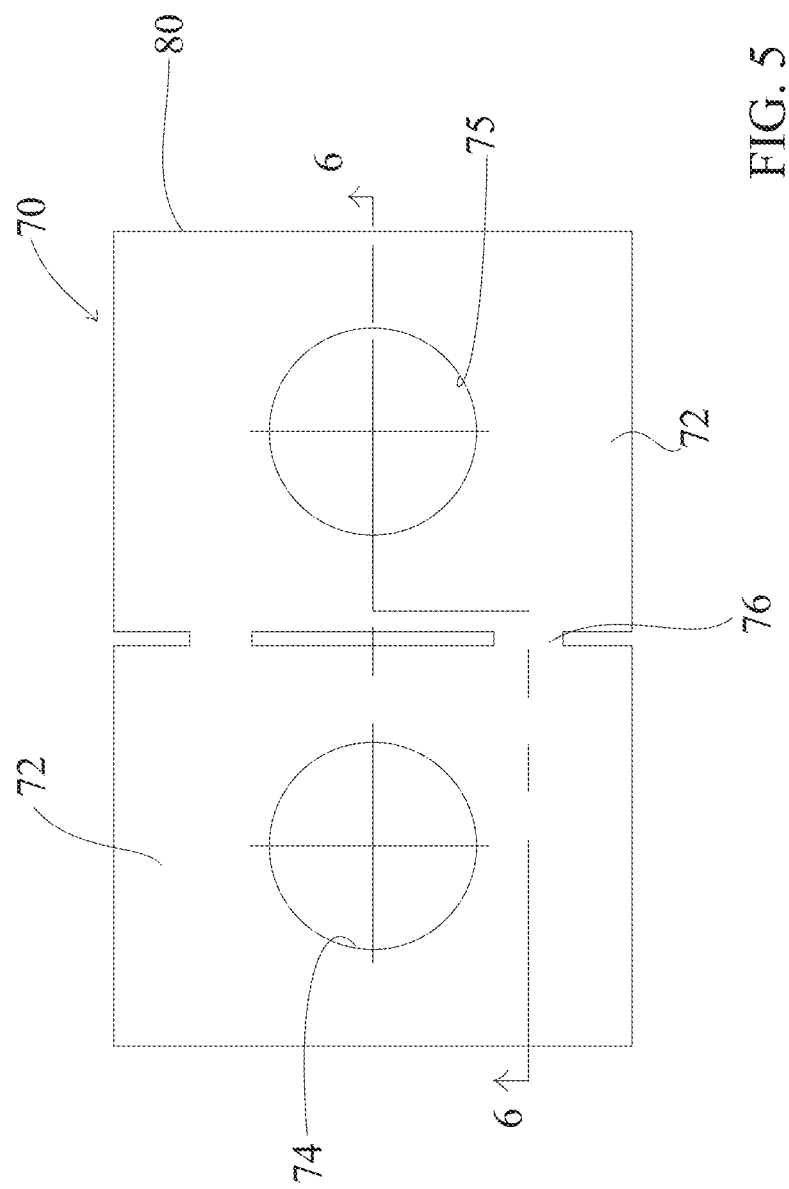

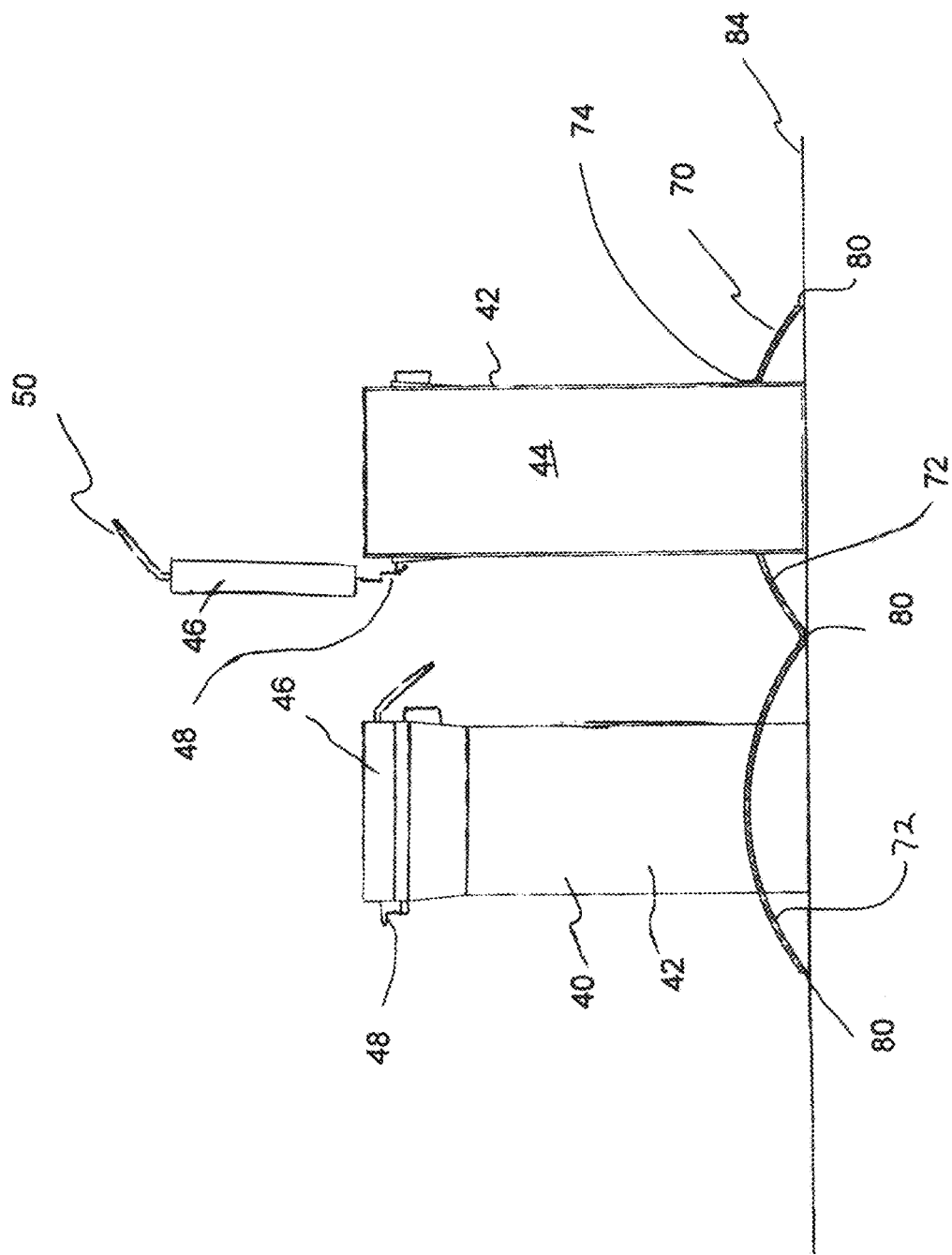

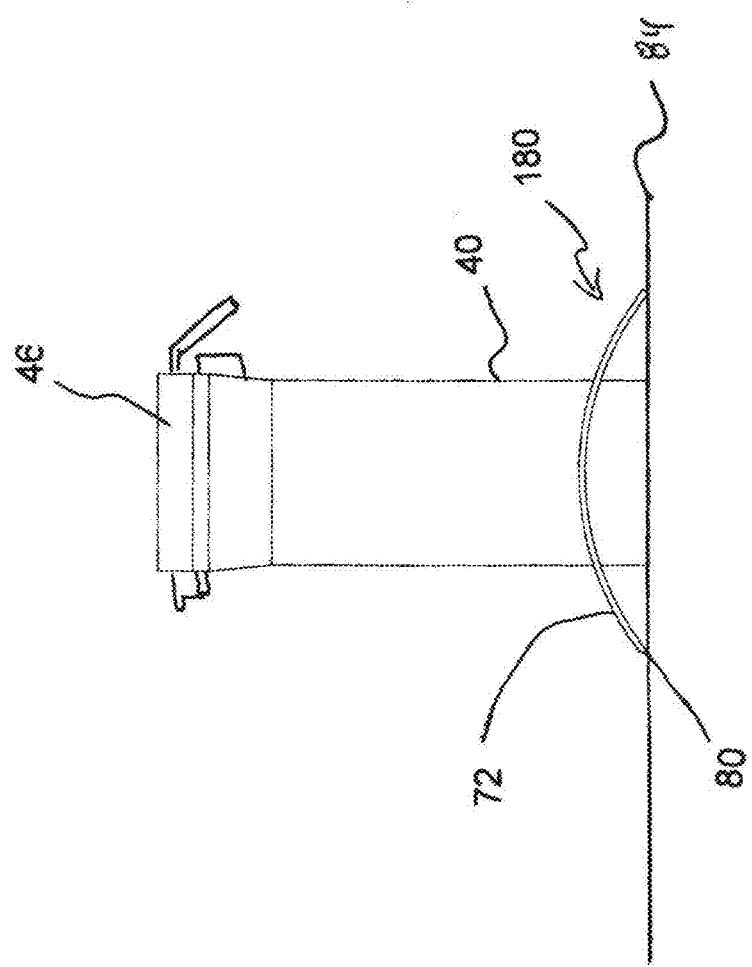

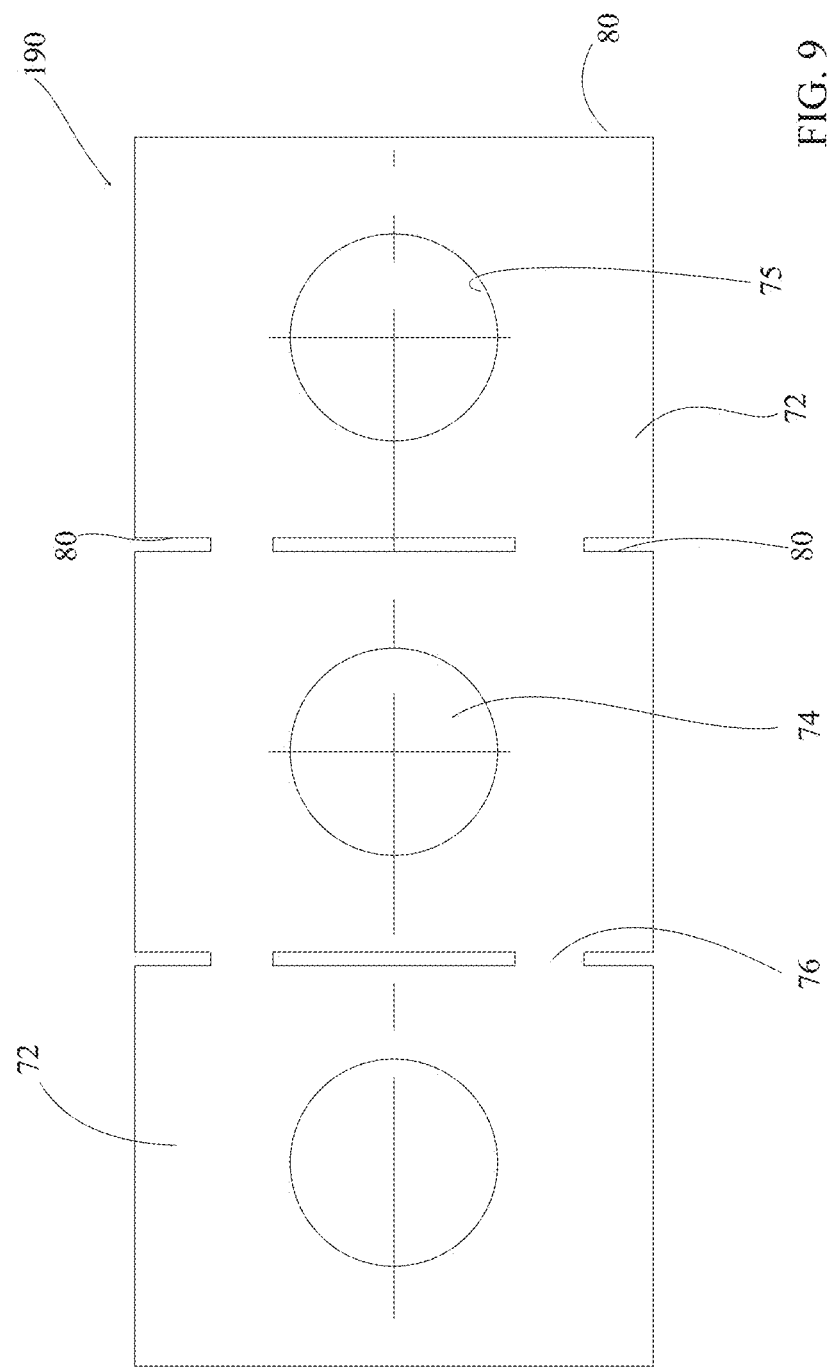

SPECIMEN COLLECTION KIT

CROSS-REFERENCE TO RELATED APPLICATION

This patent application claims the benefit of provisional application 62/213,616 filed Sep. 2, 2015, which is incorporated herein by reference.

TECHNICAL FIELD

The inventions described herein relate to a kit used for specimen collection, including a holder for a specimen bottle. More specifically, the inventions described herein include the specimen bottle holder that is disposable and can be carried within the kit for ease in packaging, storage, and transportation.

BACKGROUND

There are numerous specimens collected from humans for testing, including blood and urine. The purpose of collecting the samples can be varied including diagnosing health conditions. It is necessary that items such as bottles associated with collection not adversely affect the specimen.

In addition, there are certain occupations, such as in the transportation industry and the military, where drug testing may be required by federal law. As part of the testing there is a necessity to ensure a proper chain related to the specimen collection equipment prior to the collection of the specimen, the collection process, and after collection of the specimen, until the specimen is tested and documented at a qualified lab.

SUMMARY

It is re z for certain testing it is desirable to move the specimen from one container to another container, such as a bottle or vial. It is also recognized that it is desirable to have a holder that can hold the bottle. It is further recognized that it would be beneficial if the specimen holder could be transported as part of a collection kit.

In certain embodiments of a specimen collection kit, the kit includes a collection container adapted to receive the specimen, and a specimen bottle adapted to receive the specimen from the collection container. The kit has a specimen bottle holder having a planar plate with a bottle receiving opening to receive the specimen bottle. The specimen bottle holder has a curvature such that a pair of edges of the planar plate are adapted to engage a surface therein spacing the bottle-receiving opening from the surface.

In certain embodiments, the specimen collection kit has at least two specimen bottles. In certain embodiments, the kit has at least two bottle-receiving openings. Each bottle-receiving opening is adapted to receive the specimen bottle.

In certain embodiments, the specimen bottle holder has a pair of planar plates and a hinge interposed between the planar plates. Each of the planar plates has a curvature such that a pair of edges of the planar plate are each adapted to engage a surface therein spacing the bottle-receiving openings from the surface.

In certain embodiments, the collection container is sized to receive the specimen bottle, the specimen bottle holder, and a tamper detection packet. In certain embodiments, the tamper detection packet has a pair of pouches. The first pouch is to receive the specimen bottles and the other pouch is adapted to receive paperwork. In certain embodiments, the specimen bottle holder moves between a storage-shaped position for retaining in the collection container and a bottle-retaining position for engaging the surface and spacing the bottle-receiving openings from the surface.

In certain embodiments of a specimen bottle holder for holding a specimen bottle, the specimen bottle holder has a flexible planar plate having a bottle-receiving opening to receive the specimen bottle. The specimen bottle holder has a curvature such that a pair of edges of the planar surface are adapted to engage a surface therein spacing the bottle-receiving opening from the surface.

In certain embodiments, the specimen bottle holder has at least two bottle-receiving openings. Each bottle-receiving opening is adapted for receiving the specimen bottle.

In certain embodiments, the specimen bottle holder has a pair of for plates. The specimen bottle holder has a hinge interposed between the planar plates. Each of the planar plates has a curvature such that a pair of edges of the planar plate are adapted to engage the surface therein spacing the bottle-receiving openings from the surface.

In certain embodiments, the specimen bottle holder moves between a storage-shaped position for retaining in the collection container and a bottle-retaining position for engaging the surface and spacing the bottle-receiving openings from the surface.

It is to be understood that the features of the various embodiments described herein are not mutually exclusive and may exist in various combinations and permutations.

BRIEF DESCRIPTION OF THE SEVERAL VIEWS OF THE DRAWINGS

The foregoing and other objects, features, and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

FIG. 5 is a top view of the specimen bottle holder in a bottle-retaining position;

FIG. 6 is a sectional view of the specimen bottle holder taken along the line 6-6 in FIG. 5 and including a specimen holder;

FIG. 8 is a side view of an alternative embodiment of a specimen bottle holder; and FIG. 9 is a top view of another alternative embodiment of a specimen bottle holder.

DETAILED DESCRIPTION

The kit has multiple purposes including a method to compactly store the elements or components needed to collect a specimen. The kit needs to provide components that are needed to collect a specimen and ensure that it is easy to detect if the components have been tampered with. Finally the kit needs to provide a secure container to allow the specimen to be shipped.

Figure 1:
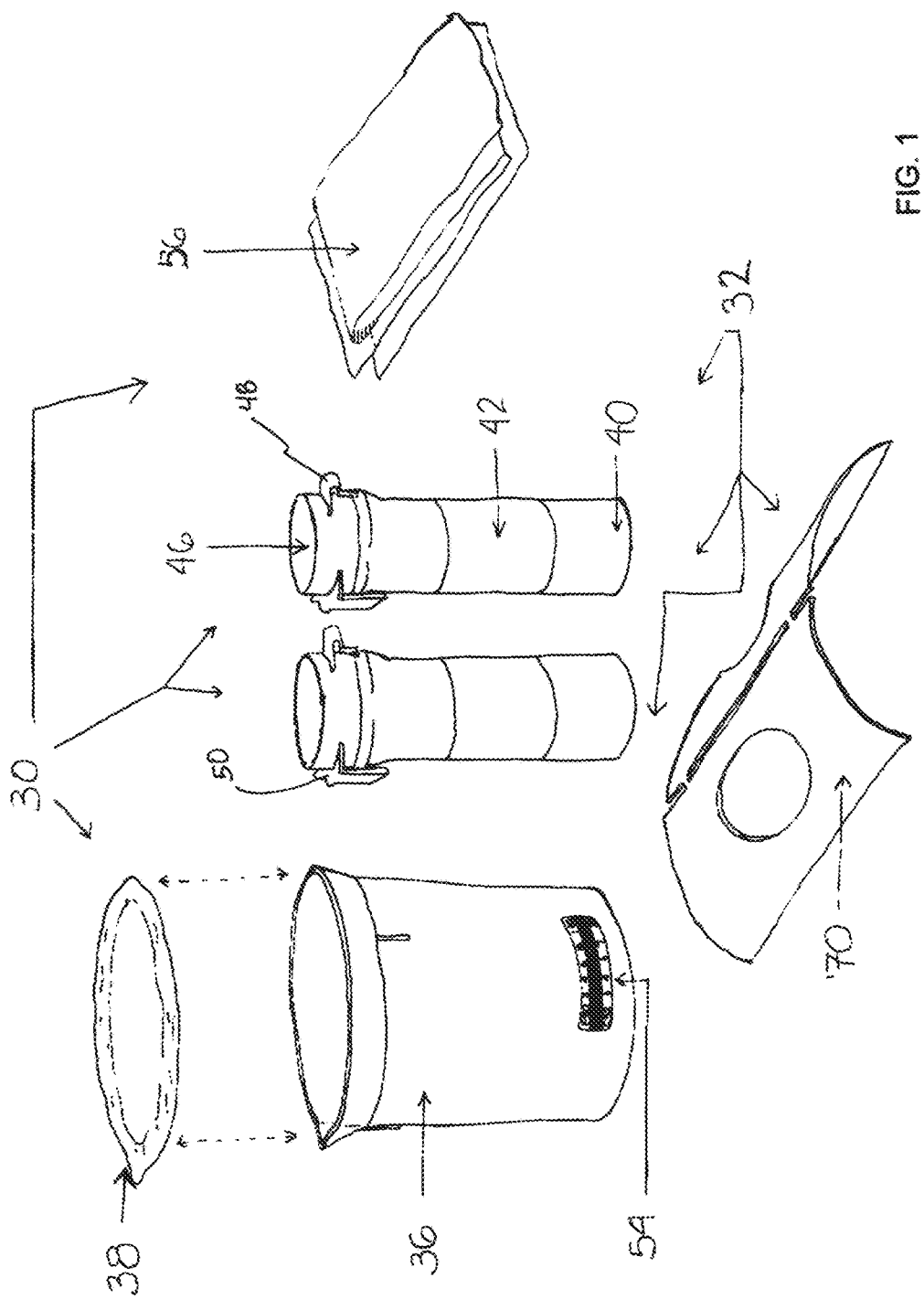
FIG. 1 is a perspective view of a kit including the components.

Referring to FIG. 1, a perspective view of a kit 30 including various components 32 is shown. While the kit 30 shows certain components 32, it is recognized that in certain embodiments the components 32 can vary. The kit 30 shown has an outer container 36 which serves several purposes including having the capability of receiving the initial specimen and also for holding the remaining components 32 for shipping and storing. The kit 30 has a lid 38 which, in the embodiment shown, is a disposable foil 38 that, is sealed to the outer container 36 to prevent contaminant from entering the other components 32 and indicating if tampering has occurred.

The kit 30 in addition has at least one bottle or specimen bottle 40 for receiving the specimen. The kit 30 shown has a pair of bottles 40. Each bottle 40 has a body 42 for receiving the specimen. The bottle 40 has a lid 46 that is secured by a flexible hinge 48 to the body 42. As explained in further detail below, the bottles 40 each have a locking securement latch 50.

Figure 7A:
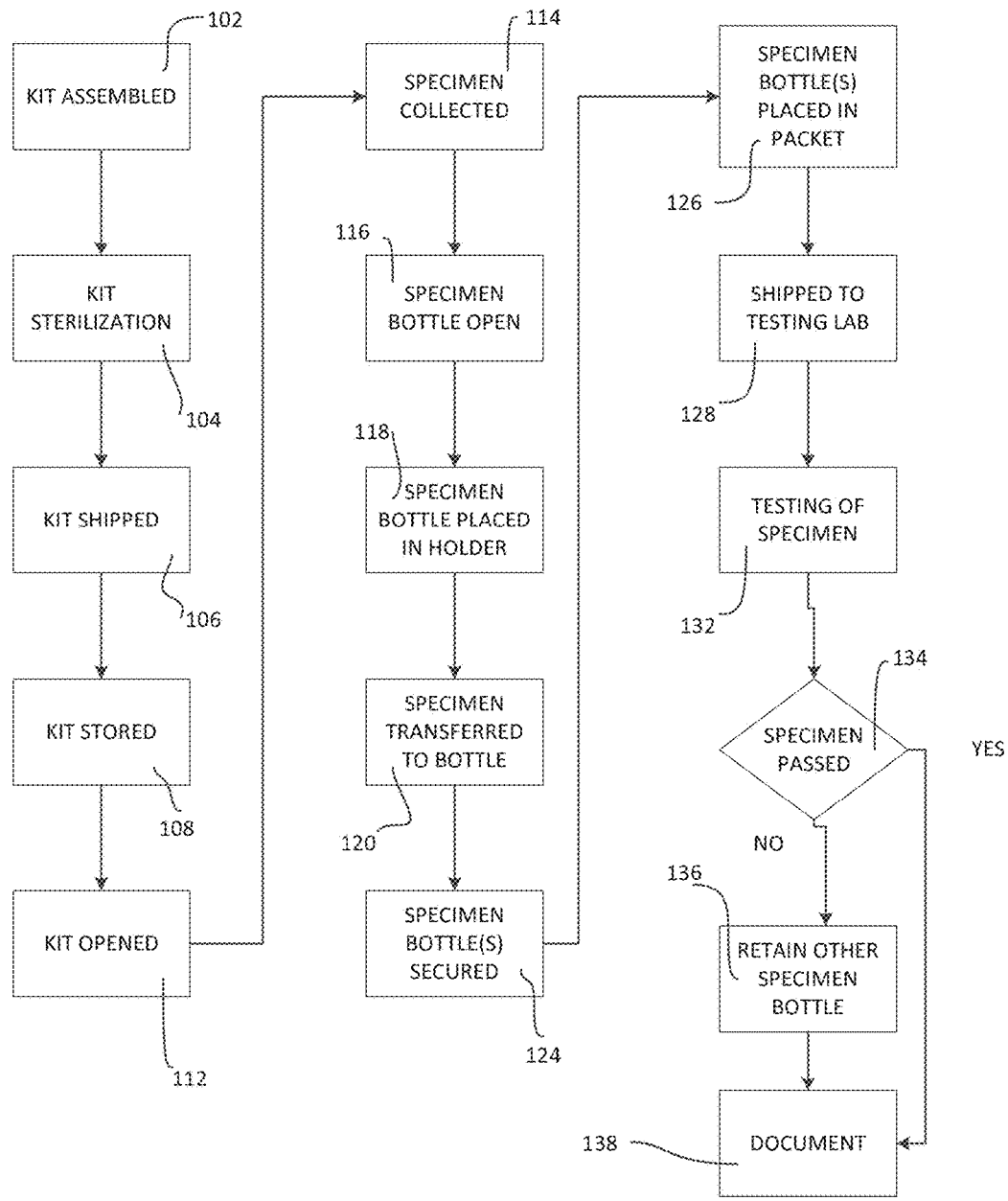
FIG. 7A is a schematic of the process of the collection of a specimen.
Figure 7B:
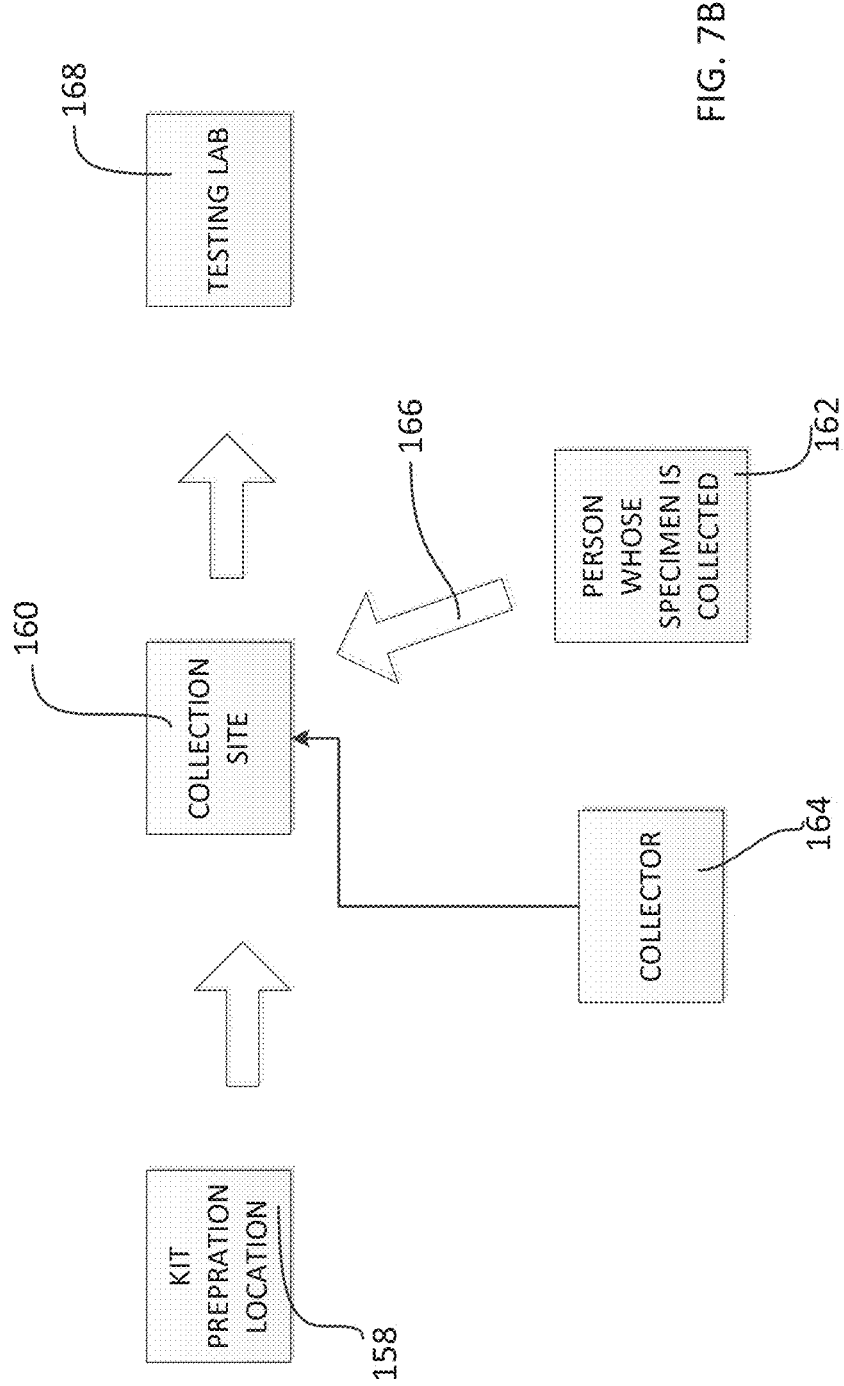
FIG. 7B is a schematic of sites related to the process of collection of the specimen.

At a collection site 160 as represented in FIG. 7B, a person 162, such as a driver for a transportation company, provides a specimen of urine for testing into the outer container 36 under some regulated observation process. The outer container 36 has a urine temperature strip 54 mounted on the outside of the outer container 36. The urine temperature strip 54 indicates a temperature between 90 degrees to 100 degrees F. in two degree increments; the strip 54 allows the collector to ensure that the temperature of the specimen received is within the conventional range.

The collector 164 is required to take the specimen 166 from the outer container 36 and place it into one or more specimen bottles or specimen vials 40. In one method of use, the collector 164 opens the bottle 40 in the presence of the person 162 providing the specimen 166. The opening of the bottle 40 in front of the person 162 providing the specimen 166 is to confirm that the bottle 40 is untainted. Once the bottle 40 is filled to a sufficient level, the lid 46 is closed to secure the specimen in the bottle 40. In certain embodiments, the bottle 40 is then covered with adhesive bottle label seals, which is an additional level of tamper detection.

Still referring to FIG. 1, the kit 30 has a tamper detection packet 56 that is adapted to receive the bottles 40. The packet 56 has a pair of pouches. The specimen bottles 40 are placed in one of the pouches. The tracking paper is placed in the other pouch of the tamper detection packet 56. The tamper detection packet 56 is shipped using proper methods to a testing facility or lab 168.

One of the difficulties that the collector 164 experiences is ensuring that the bottle 40 does not tip as the collector 164 is placing the specimen 166 in the bottle 40. The kit 30 has a bottle holder 70 to retain the bottles in an upright position 40 when the collector 164 is placing the specimen 166 in the bottle 40 from the outer container 36.

Figure 2:
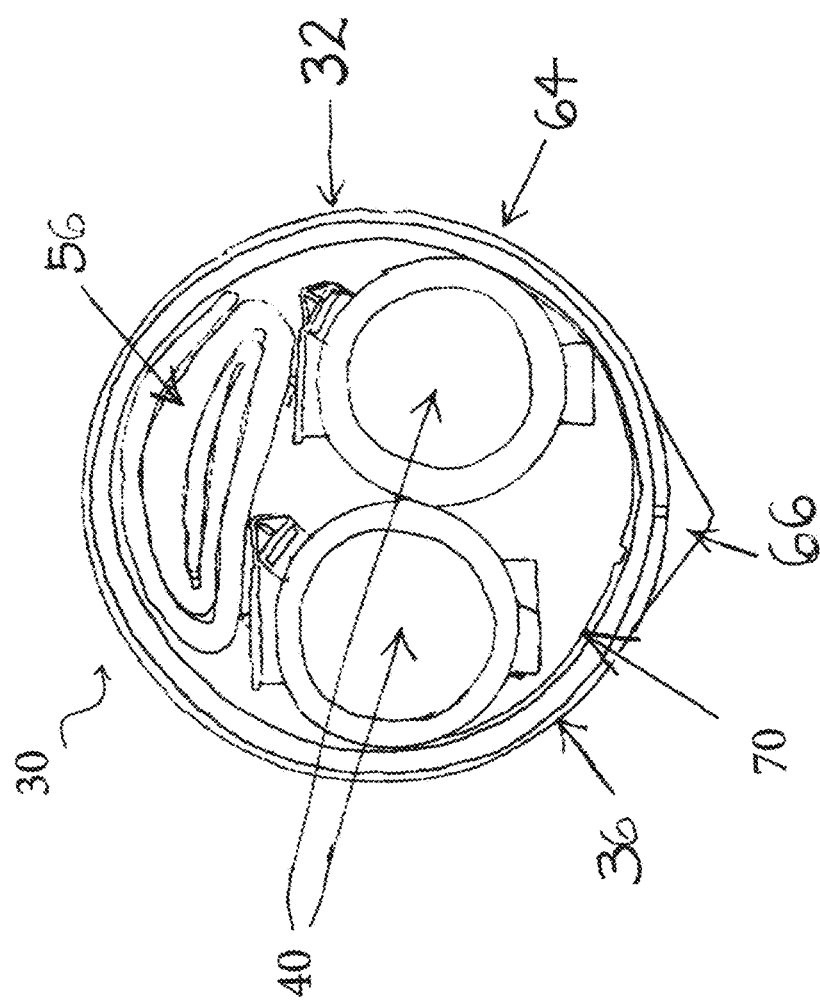
FIG. 2 is a top view of a kit with the components.

Referring to FIG. 2, a top view of the kit 30 with the components 32 is shown. As indicated above, the kit 30 holds the components 32 in a compact condition to store the elements needed to collect a specimen 166. The outer container 36 has an outer wall 64 and a pouring spout 66 to facilitate the pouring of the specimen from the outer container 36 into the bottles 40. The two bottles 40 are shown within the outer container 36. The tamper detection packet 56 is shown in a space of the outer container 36 not occupied by the bottles 40. The bottle holder 70 is interposed between the wall 64 of the outer container 36 and the two bottles 40. The lid 46 shown in FIG. 1 would be covering the opening or the outer container 36 during transportation and storage prior to being opened by the collector in the presence of the person providing the specimen.

Figure 3:
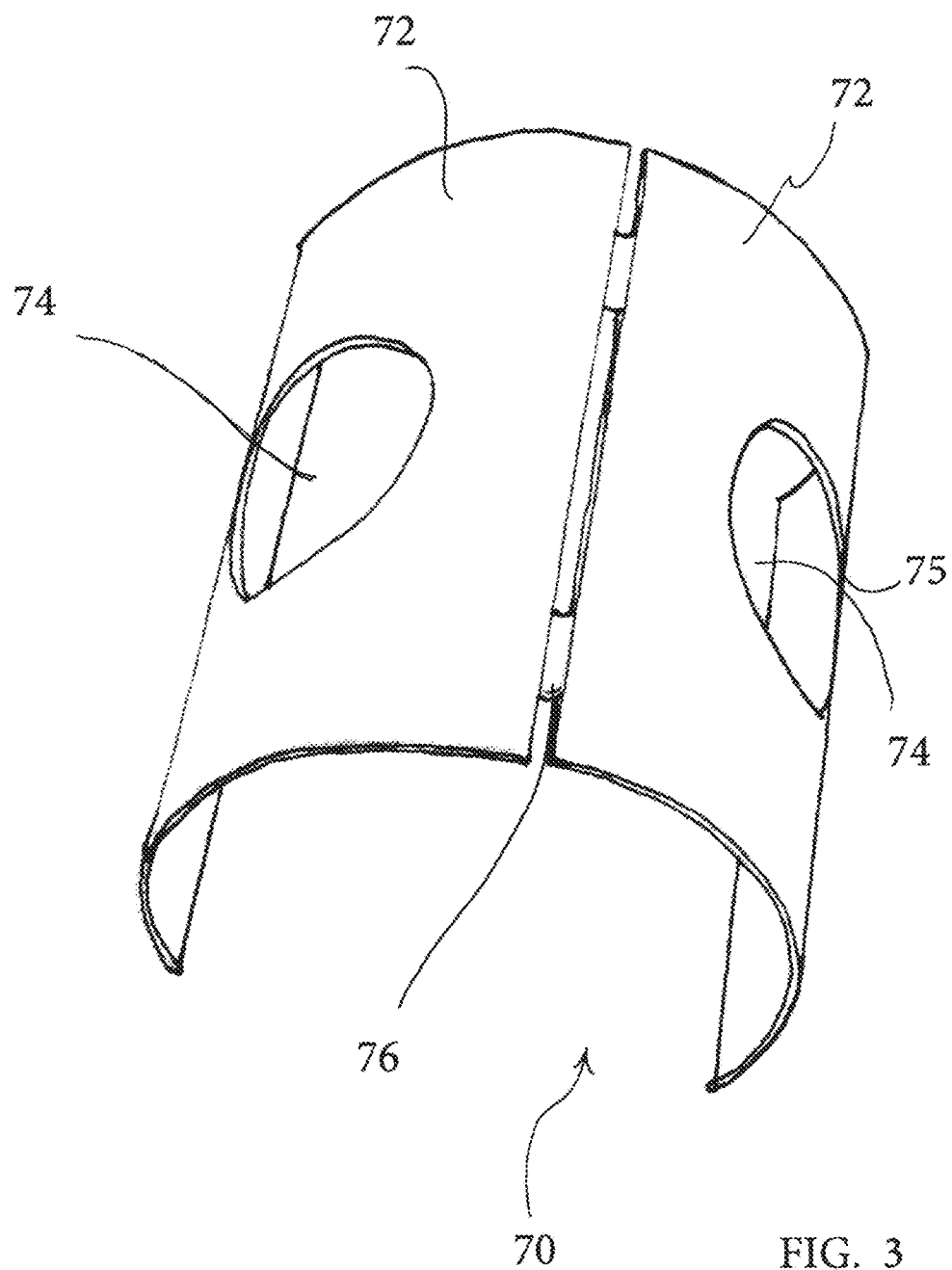
FIG. 3 is perspective view of a specimen bottle holder in a storage-shaped position.

Referring to FIG. 3, a perspective view of a specimen bottle holder 70 in a storage-shaped position is shown. The specimen bottle holder 70 has generally a planar shape and is flexible and is capable of curving to be stored and transported in the outer container 36 of the kit 30. The specimen bottle holder 70 a pair of planar plates or panels 72. Each of the panels 72 of the specimen bottle holder 70 has a bottle-receiving opening 74 adapted each to receive a bottle 40. The bottle-receiving opening 74 is defined by an opening edge 75 of the panel 72 of the specimen bottle holder 70. The specimen bottle holder 70 has a pair of living or flexible hinges 76 between the pair of panels 72.

Figure 4A:
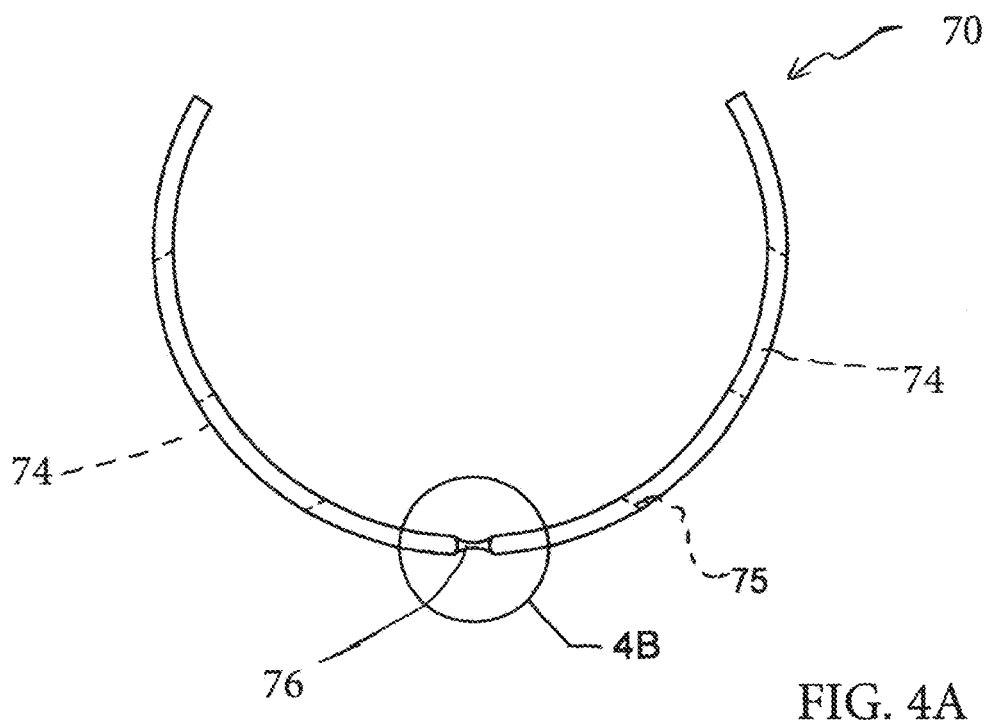
FIG. 4A is a side view of the specimen bottle holder in the storage-shaped position.

Referring to FIG. 4A, a side view of the specimen bottle holder 70 in the storage-shaped position is shown. The two bottle-receiving openings 74 are shown in hidden line. While the specimen bottle holder 70 is shown in a shape to conform to the outer container 36 of FIG. 1 and FIG. 2, it is recognized that the specimen bottle holder 70 could have a different, shape and/or radius of curvature to fit a different, diameter of the outer container 36.

Figure 4B:
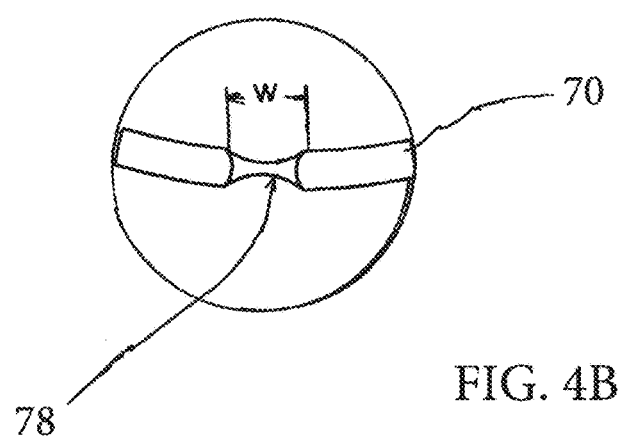
FIG. 4B is an enlarged view of a hinge of the specimen bottle holder taken at 4B in FIG. 4A.

The living or flexible hinge 76 between the pair of panels 72 is shown. Referring to FIG. 4B, an enlarged view of a hinge 76 of the specimen bottle holder 70 taken at 4B in FIG. 4A is shown. The living hinges 73 narrow from the two panels 72 to a necked portion 78 to increase flexibility of the hinges 76. In that the specimen bottle holder 70 in certain embodiments is formed of a flexible material, the panels 72 in addition to the hinges 76 have flexibility.

In certain embodiments, the specimen bottle holder 70 has a thickness of 1 millimeter. The bottle-receiving openings 74 are sized to receive the bottles 40 and have a diameter of 15 millimeters. The living hinge 76 has a width w of 2 millimeters and necks down to a thickness of 0.6 millimeter.

The specimen bottle holder 70 is formed of a plastic that is capable of being subjected to sterilization. While it is not expected that the specimen bottle holder 70 is going to make contact with the specimen, the specimen bottle holder 70 needs to be capable of being subject to treatment when the sealed kit 30 is processed prior to shipping to the collection site 160. The treatment is to ensure that surfaces such as the inside of the outer container 36 and the bottle 40 are capable of receiving the specimen without tainting the specimen. In that the specimen bottle holder 70 is disposed after the specimen is moved from the outer container 36 to the sample bottle 40, it is desirable at least in certain embodiments to produce a specimen bottle holder 70 cheaply of materials that can be recycled subject to medical waste issues.

In certain embodiments, the specimen bottle holder 70 is formed using a 3D printing using fused deposition modeling (filament printing) process with the filament made of ABS (Acrylonitrile Butadiene Styrene), PLA (Polylactic Acid), or PVA (Polyvinyl Alcohol). In other embodiments, the specimen bottle holder 70 is formed of a clear polystyrene, PVC, nylon, or a material identical to the specimen container or bottle 40. In certain embodiments, the specimen bottle holder 70 is formed of compressed paper.

Referring to FIG. 5, a top view of the specimen bottle holder 70 in a bottle-retaining position is shown. The specimen bottle holder 70 is placed on a flat surface 84 as seen in FIG. 6. The specimen bottle holder 70 has a generally planar shape and has a pair of panels 72. Each of the panels 72 of the specimen bottle holder 70 has a bottle-receiving opening 74 adapted each to receive a bottle 40. The specimen bottle holder 70 has a pair of living hinges 76 between the pair of panels 72.

Referring to FIG. 6, a sectional view of the specimen bottle holder 70 taken along the line 6-6 in FIG. 5A is shown. A specimen bottle 40 is shown in each of the bottle-receiving openings 74. The specimen bottle 40 on the left side of FIG shows the outside of the specimen bottle 40 including the body 42 and the lid 46 and the interposed flexible hinge 48. The specimen bottle 40 on the right side of FIG. shows a sectional view of the specimen bottle 40 in the bottle-receiving opening 74.

The panels or planar plates 72 each have a pair of surface engaging edges 80. The surface engaging edges 80 each engage the flat surface 84. One of the surface engaging edges 80 has the living hinges 76 which engage the flat surface 84. The bottle-receiving openings 72 are spaced from the flat surface 84. The bottles 40 are supported by the flat surface 84 and the edge of the bottle-receiving openings 72 of the specimen bottle holder 70. The curvature of the planar panels of the specimen bottle holder 70 results in the bottle-receiving openings 72 being spaced from the flat surface 84; the spacing of the bottle-receiving openings 72 from the flat surface 84 increases stability.

Referring to FIG. 7A, a schematic of the process of collection of a specimen is shown. The components 32 of the kit 30 are assembled as represented by block 102. The kit 30 is processed to ensure the kit meets requirements including sterilization as represented by block 104. The kit 30 is shipped to the collection area or site 160 as represented by block 106. The kit 30 is stored until needed as represented by block 108. While one kit 30 is referenced, the kits 30 are typically bundled to this point for handling.

When a person 162 whose specimen 166 is required is ready for the specimen collection, the collector 164 opens the kit 30 in front of the person 162 whose specimen 166 is required by removing the lid 38 of the outer container 36. The components 32 located in the outer container 36 are removed including the specimen bottles 40 and the specimen bottle holder 70 as represented by block 112.

The outer container 36 is used to collect the specimen from the person 162 whose specimen 166 is required as represented by block 114. The specimen bottles 40 are opened and shown to the person 162 whose specimen 166 is required as represented by block 116.

The specimen bottles 40 are placed in the specimen bottle holder 70 as represented by block 118. The specimen bottle holder 70 has a curvature of the planar panels 72 such that the bottle-receiving openings 72 are spaced from the flat surface 84.

The specimen 166 is transferred from the outer container 36 to the specimen bottles 40 as represented by block 120. The pouring spout 66 of the outer container 36 facilitates the transfer. While the collector 164 can be wearing gloves, it is typically desirable to have the specimen bottle 40 positioned in a stabilized manner; the specimen bottle holder 70 with the curvature engages points of the specimen bottle 40 that are spaced: the flat surface 84 and the edge 75 of the bottle-receiving opening 74.

Once the specimen 166 is transferred to the specimen bottles 40, the lids 38 of the specimen bottles 40 are closed. The specimen bottles 40 are secured to prevent leakage of the specimen. In addition, the locking securement latch 50 of the specimen bottle 40 is moved to a secure position such that tampering can be detected. The specimen bottle 40 is secured as represented by block 124. In certain embodiments, a specimen bottle seal is placed over the closure and down the sides, and may include requirements to write the date and initials of the donor on the seal.

The specimen bottles 40 are placed in one of the pouches of the tamper detection packet 56. In addition, the paperwork is placed in the other of the pouches of the tamper detection packet 56 as represented by block 126.

The specimen bottles 40 are shipped to a testing lab 168 as represented by block 128.

The specimen 166 in one of the specimen bottles 40 is tested at the testing lab 168 as represented by block 132. If the specimen passes, as represented by the yes branch of decision diamond 134, the testing is documented as represented by block 138.

If the first specimen fails or is otherwise noted as a non-proper specimen as represented by the no branch of the decision diamond 134, the other specimen bottle 40 is retained as represented by block 136. The testing is documented as represented by block 138.

Referring to FIG. 7B, a schematic of sites related to the process of collection of the specimen is shown. The kits 30 for collection and shipping of the specimen 166 move through various locations. The components 32 of the kit 30 are prepared at a kit preparation site 158. The preparation site 158 can include multiple locations including distinct locations for assembly and treating for processing such as sterilization.

The kits 30 are sent to the collection site 160 such as represented by block 106 in FIG. 7A. It is expected that collection sites 160 are located at various locations such as at least a location in each state. The person 162 whose specimen 166 is required provides a specimen 166 into the outer container 36. The collector 164 using the specimen bottle holder 70 to hold the specimen bottle 40, transfers the specimen 166 to the specimen bottles 40. The bottles are sealed and packaged and shipped to a testing lab 168.

As indicated above, one of the specimen bottles 40 is tested and documented. Depending on the result of the specimen 166 in the first specimen bottle 40, the second specimen bottle 40 is either retained or disposed.

Referring to FIG. 8, a top view of an alternative embodiment of a specimen bottle holder 180 is shown. The alternative specimen bottle holder 180 has a single planar portion 72 with a single bottle-receiving opening 74

Referring to FIG. 9, a top view of another alternative embodiment of a specimen bottle holder 190 is shown. The specimen bottle holder NO has three panels 72 such that each has a bottle-receiving opening 74. Each of the planar panels 72 has a pair of surface engaging edges 80.

EQUIVALENTS

The invention may be embodied in other specific forms without departing from the spirit or essential characteristics thereof. The foregoing embodiments are therefore to be considered in all respects illustrative rather than limiting on the invention described herein. The true scope of the invention is thus indicated by the descriptions contained herein, as well as all changes that come within the meaning and ranges of equivalency thereof.

It is recognized that in certain embodiments, a planar portion of the specimen bottle holder has two or more bottle receiving 74 that are aligned parallel with one of the surface engaging edges.

What is claimed is:

1. A specimen collection kit comprising:
a collection container adapted to receive the specimen;

a specimen bottle adapted to receive the specimen from the collection container; a specimen bottle holder having a planar plate with a bottle-receiving opening to receive the specimen bottle, the specimen bottle holder having a curvature such that a pair of edges of the planar plate are adapted to engage a surface therein spacing the bottle-receiving opening from the surface; wherein the collection container is sized to receive the specimen bottle and the specimen bottle holder, the specimen bottle holder movable between a storage-shaped position having a curvature of the collection container for retaining in the collection container and a bottle-retaining position for engaging the surface and spacing the bottle-receiving opening from the surface.

2. A specimen collection kit of claim 1 wherein the specimen bottle is at least two specimen bottles.

3. A specimen collection kit of claim 2 wherein the specimen bottle holder has at least two bottle-receiving openings, each bottle-receiving opening to receive the specimen bottle.

4. A specimen collection kit of claim 3 wherein the specimen bottle holder has a pair of planar plates, the specimen bottle holders having a hinge interposed between the planar plates, each of the planar plates having a curvature such that a pair of edges of the planar plate are adapted to engage the surface therein spacing the bottle-receiving openings from the surface.

5. A specimen collection kit of claim 1 further comprises a tamper detection packet having a pair of pouches, the first pouch to receive the specimen bottles and the other pouch adapted to receive documentation.

6. A urine specimen collection kit for collection of the urine specimen and adapted to work with a flat surface, the collection kit comprising:
a collection container adapted to receive the specimen;
a pair of specimen bottles adapted to receive the specimen from the collection container;
a specimen bottle holder having a planar plate with a bottle-receiving opening to receive the specimen bottle, the specimen bottle holder having a curvature such that a pair of edges of the planar plate are adapted to engage the flat surface therein spacing the bottle-receiving opening from the surface, wherein the specimen bottle holder moves between a storage-shaped position for retention in the collection container and a bottle-retaining position for engaging the surface and spacing the bottle-receiving opening from the surface; and wherein the collection container is sized to receive the specimen bottle, the specimen bottle holder, and a tamper detection packet, wherein the collection container is sized to receive the specimen bottle and the specimen bottle holder, the specimen bottle holder movable between a storage-shaped position having a curvature of the collection container for retaining in the collection container and a bottle-retaining position for engaging the surface and spacing the bottle-receiving opening from the surface.

7. A specimen collection kit of claim 6 wherein the specimen bottle holder has at least two bottle-receiving openings, each bottle-receiving opening to receive the specimen bottle.

8. A specimen collection kit of claim 7 wherein the specimen bottle holder has a pair of planar plates, the specimen bottle holder having a hinge interposed between the planar plates, each of the planar plates having a curvature such that a pair of edges of the planar plate are adapted to engage the surface therein spacing the bottle-receiving openings from the surface.

9. A specimen collection kit of claim 6 wherein the tamper detection packet has a pair of pouches, the first pouch to receive the specimen bottles and the other pouch adapted to receive documentation.

10. A specimen collection kit of claim 8 wherein the hinge interposed between the planar plates is a pair of living hinges.

11. A specimen collection kit of claim 6 further comprises a urine temperature strip mounted on the outside of the collection container.

12. A specimen collection kit of claim 6 wherein the collection container has an outer diameter having a pouring spout projecting outward from the outer diameter of the collection container to facilitate the pouring of the specimen from the collection container to the specimen bottle.

13. A specimen collection kit of claim 1 wherein the specimen bottle holder is brined of a plastic capable of being subjected to sterilization.

14. A urine specimen collection kit of claim 6 wherein the specimen bottle holder is formed of a plastic capable of being subjected to sterilization.

* * * * *